(12) United States Patent
Tschirren et al.

(10) Patent No.: US 12,714,801 B2
(45) Date of Patent: Aug. 25, 2026

(54) AUTOINJECTOR HAVING A DISCHARGE-RELEASE MEANS

(71) Applicant: Ypsomed AG, Burgdorf (CH)

(72) Inventors: Markus Tschirren, Burgdorf (CH); Gabriel Kalbermatter, Burgdorf (CH); Leos Urbanek, Bern (CH); Marcel Allenspach, Burgdorf (CH)

(73) Assignee: Ypsomed AG, Burgdorf (CH)

( * ) Notice: Subject to any disclaimer, the term of this patent is extended or adjusted under 35 U.S.C. 154(b) by 876 days.

(21) Appl. No.: 17/971,076

(22) Filed: Oct. 21, 2022

(65) Prior Publication Data

US 2023/0050314 A1 Feb. 16, 2023

Related U.S. Application Data

(63) Continuation of application No. PCT/EP2021/059856, filed on Apr. 16, 2021.

(30) Foreign Application Priority Data

Apr. 22, 2020 (EP) .................................... 20170759

(51) Int. Cl.

*A61M 5/31* (2006.01)
*A61M 5/20* (2006.01)
*A61M 5/315* (2006.01)

(52) U.S. Cl.

CPC ...... *A61M 5/31578* (2013.01); *A61M 5/2033* (2013.01); *A61M 5/31591* (2013.01); *A61M 2005/2013* (2013.01)

(58) Field of Classification Search

CPC ........ A61M 2005/2013; A61M 5/2033; A61M 5/31578

See application file for complete search history.

(56) References Cited

U.S. PATENT DOCUMENTS

2016/0116184 A1 4/2016 Chappell et al.
2018/0110926 A1* 4/2018 Schrul ................ A61M 5/3159
(Continued)

FOREIGN PATENT DOCUMENTS

EP 1728529 A1 12/2006
EP 3900759 A1 10/2021
(Continued)

OTHER PUBLICATIONS

International Preliminary Report on Patentablity issued in International Application No. PCT/EP2021/059856, 7 pages.
(Continued)

*Primary Examiner* — William R Carpenter
(74) *Attorney, Agent, or Firm* — Dorsey & Whitney LLP

(57) ABSTRACT

An autoinjector including a housing; an axially fixed product container; a torsion spring; a drive element; a propulsion element; and a needle protection sleeve is configured such that when the autoinjector is pressed against an injection location, the needle protection sleeve undergoes an actuation movement in the proximal direction. For discharging liquid from the product container through an injection needle into the injection location, the torsion spring sets the drive element into rotation and the rotating drive element causes a movement of the propulsion element and a piston in the product container in the distal direction. The autoinjector includes a coupling which, due to the actuation movement of the needle protection sleeve, releases the drive element for rotation, where the coupling is between a first and second coupling element in an engagement of locking surfaces, and can be disengaged by an axial coupling stroke of the two coupling elements.

22 Claims, 6 Drawing Sheets

(56) References Cited

U.S. PATENT DOCUMENTS

| | | | | |
|---|---|---|---|---|
| 2018/0169346 | A1* | 6/2018 | Hostettler | A61M 5/1454 |
| 2020/0171246 | A1* | 6/2020 | Byerly | A61M 5/20 |

FOREIGN PATENT DOCUMENTS

| | | | |
|---|---|---|---|
| WO | 2009037141 | A1 | 3/2009 |
| WO | 2016205963 | A1 | 12/2016 |
| WO | 2017089254 | A1 | 6/2017 |
| WO | 2016205961 | A8 | 2/2018 |
| WO | 2018100126 | A1 | 6/2018 |
| WO | 2020164910 | A1 | 8/2020 |
| WO | 2021213901 | A1 | 10/2021 |

OTHER PUBLICATIONS

European Search Report issued in European patent application No. 20170759.3, issued on Nov. 9, 2020, 9 pages.

International Search Report and Written Opinion issued in International Application No. PCT/EP2021/059856, issued on Jun. 29, 2021, 15 pages including 3 pages of English translation.

* cited by examiner 21c
18
24b
22b
21c

AUTOINJECTOR HAVING A DISCHARGE-RELEASE MEANS

CROSS REFERENCE TO RELATED APPLICATIONS

This application claims priority to International Patent Application No. PCT/EP2021/059856, filed Apr. 16, 2021, entitled "AUTOINJECTOR HAVING A DISCHARGE-RELEASE MEANS," which in turn claims priority to European Patent Application No. 20170759.9, filed Apr. 22, 2020, entitled "AUTOINJECTOR HAVING A DISCHARGE-RELEASE MEANS," each of which is incorporated by reference herein, in their entirety and for all purposes.

TECHNICAL FIELD

The present disclosure relates to the field of medical injection devices for administering liquid substances including medications or medical substances such as insulin and hormone preparations, and discloses an autoinjector with an energy store for discharging a predetermined dose from a single-use product container.

BACKGROUND

Injection devices or injection apparatuses for the simplified administration of a substance inter alia include so-called autoinjectors which have an energy store with which the discharge process can be carried out automatically, i.e., without a force to be supplied or exerted externally by a user. The energy store may store the energy required for an automatic substance delivery in mechanical form. Such an energy store may be a spring which is installed in a tensioned state in the injection device and delivers energy by expansion. The energy is delivered to a piston rod or a pressure element, which pushes a piston into a product container. The energy store may also be provided in order to automate the process of inserting an injection needle. Alternatively, the insertion process may take place manually, i.e., exclusively by a user, without using energy stored in the injection device for this purpose.

The injection device may include a product container holder for accommodating a product container, where the product container may be held in the product container holder radially, axially, and also in a rotationally fixed manner. The product container holder may be connected to the housing of the injection apparatus in an axially and rotationally fixed manner or may be movable relative to the housing during an insertion and/or needle retraction process. The product container may be a carpule with a septum for a one-time or repeated connection to a disposable injection needle, or may be a disposable, ready-to-use, pre-filled syringe with an injection needle non-detachably connected thereto. The product container has a hollow cylindrical product container portion, which displaceably mounts a piston or plunger. The piston may form a sealing gap with the inner circumference of the product container portion and may be displaced in a distal direction by means of a piston rod in order to dispense product from the product container via the injection needle.

The injection device may have a needle protection sleeve, which after an injection has taken place, projects distally beyond a distal end of the injection needle or is displaced relative to the housing into this position while expanding a needle protection sleeve spring, in order to prevent accidental access to the injection needle and to thereby reduce the risk of injury. In an autoinjector, the needle protection sleeve may also serve as a trigger element for triggering the product discharge process, where the needle protection sleeve is displaced relative to the housing in the proximal direction for this purpose. Alternatively, triggering of the autoinjector may be achieved by actuating a trigger button of the autoinjector, where the needle protection sleeve serves at least as a visual protection before the autoinjector is used.

WO 2016/205963 A1 describes an exemplary autoinjector including a housing with a longitudinal axis and a product container arranged axially fixedly in the housing. The autoinjector furthermore includes a needle protection sleeve, which is displaceable in a longitudinal direction between a proximal and a distal position and is coupled to a needle protection spring. A spiral spring or mainspring in which energy for the automatic discharge of product can be stored is connected via a first end to the housing, and via a second end is connected in a rotationally fixed manner to a drive element in the form of a rotating threaded rod arranged coaxially with the longitudinal axis. The threaded rod engages via a thread in a propulsion member in the form of a propulsion sleeve, which propulsion member is not rotating in the housing and which propulsion sleeve moves the plunger of the product container at an at least approximately constant discharge rate in the distal direction during a displacement. Before discharge, a holding element with two flexible holding arms engages in recesses of the propulsion member and prevents a movement of the latter. The arms of the holding element are held in the engagement by a locking sleeve. When the discharge is triggered, the locking sleeve is moved away from the position of the recesses by a proximal movement of the needle protection sleeve so that the holding arms can detach radially and release the propulsion member. Before discharge and in some circumstances over the course of several years, the torque of the spiral spring is applied via the drive element to the proximal end of the propulsion member and the propulsion force is applied to the holding element, which leads to a static material load on the propulsion member and the holding arms and can result in possible fatigue phenomena.

WO 2009/037141 A1 describes an autoinjector with a syringe movement for highly viscous medicaments, in which a needle protection sleeve during placement onto the injection site pushes a trigger sleeve in the proximal direction by a small release stroke, thereby releasing a radial toothing between the trigger sleeve and a drive member. The drive member is driven by a spiral spring and, via a threaded connection with a proximal thread of an internal piston rod, pushes the latter in the axial direction, which ensures first an automatic piercing movement and then a medicament discharge. The piston rod furthermore includes a distal part having a larger diameter than the thread-bearing proximal part of the piston rod.

WO 2017/089254 A1 describes an autoinjector with a mainspring, which is released by the user from the outside via an engagement at the proximal end of a threaded rod.

SUMMARY

Disclosed are autoinjectors and torsion spring drives for such autoinjectors for automatically discharging a liquid from a ready-to-use syringe (e.g., a pre-filled syringe), which may be fixed in the autoinjector housing and in which a torque of the torsion spring is reliably blocked or absorbed until discharge is desired.

Autoinjectors according to the present disclosure may include a one-piece or multi-part housing with a longitudinal axis that is configured to receive a ready-to-use syringe (e.g., a pre-filled syringe) with a product container and an injection needle or cannula, and which may be non-detachably fastened thereto. For instance, the ready-to-use syringe may be axially, non-displaceably accommodated in the housing, where a tip of the injection needle projects by a piercing depth in the distal direction beyond a distal housing end. The autoinjector furthermore may include a torsion spring pretensioned for the single discharge of a maximum content of the product container, a drive element, a propulsion element, and a needle protection sleeve. For discharging liquid from the product container through the injection needle, the torsion spring may set the drive element into rotation about the longitudinal axis, and the rotating drive element may thereby cause a linear movement of the propulsion element to displace a piston in the product container. When the autoinjector is pressed against an injection site resulting in the injection needle piercing the injection site, the needle protection sleeve may be moved in the proximal direction by an actuation stroke, thereby starting or enabling a discharge of liquid. The actuation stroke of the needle protection sleeve may correspond to at least the piercing depth of the injection needle.

The autoinjector may further include a coupling, which may not include or involve the propulsion element and which may be independent of the propulsion element, with coupling elements that may differ only from the propulsion element, which coupling may block a rotation of the drive element before the discharge and, as a result of the movement of the needle protection sleeve during piercing, may release, for rotation, the drive element or a rotational element connected thereto in a rotationally fixed manner. The coupling thus may not block the linear movement of the propulsion element but may directly block the torque of the torsion spring on the drive element. This may prevent the rotationally fixed connection or coupling of the drive element and propulsion element from being loaded during the entire storage period of the autoinjector and from thereby possibly being damaged.

In implementations, all coupling elements of the coupling may be located distally or on the needle-protection-sleeve-side of the torsion spring so that the drive element does not extend beyond a proximal end of the torsion spring. Furthermore, a recess in the propulsion element for the engagement of a holding element may not be required; as a result, during assembly, the propulsion element can be screwed onto a thread to a different extent corresponding to an intended discharge stroke or an axial starting position of the plunger. For partially filled ready-to-use syringes, the propulsion element may not be screwed over the entire length of the gear, as a result of which fractions of a maximum discharge stroke are easily adjustable.

In implementations, the coupling may include a first, inward directed coupling element, which may selectively engage in a second, outward directed coupling element via locking surfaces which act against rotation about the longitudinal axis and are aligned in parallel to the longitudinal axis, where this engagement may be released by an axial coupling stroke or an axial relative movement of the first and second coupling elements. Due to this axial movement, no additional space may be required radially in the autoinjector, in contrast to radial decoupling in which a first coupling element is moved away from a second coupling element in the radial direction.

The coupling stroke may take place manually or in a spring-assisted manner; without a transmission ratio, the coupling stroke may correspond to an actuation stroke of the needle protection sleeve during piercing, and thus to at least one piercing depth of the injection needle, which for its part is may be least 3 mm or at least 5 mm. The torque of the torsion spring may be blocked or absorbed via the coupling elements with locking surfaces parallel to the longitudinal axis of the autoinjector. An axial length of these locking surfaces may fall below a length of the coupling stroke, and for instance may be at least 2 mm, or at least 4 mm, and may likewise correspond to at least the piercing depth.

In implementations, the propulsion element may include a non-rotationally symmetrical cross-section with an axial guide element in the form of a groove, plane, or rib parallel to the longitudinal axis, via which the propulsion element may be guided axially linearly through the housing or a guide counterelement which is accommodated in a rotationally fixed manner in the housing. The propulsion element may be coupled via a thread to the drive element and may move exclusively axially in the discharge direction and not, for example, in a screwing propulsion movement. As a result, friction between a distal end face of the propulsion element and the piston may be avoided, and it may moreover be easier to provide the drive element and/or the propulsion element with a thread that is adapted for generating a changed discharge force or with a special threaded surface coating than the housing. When the propulsion element is screwed into or onto the thread of the drive element, the propulsion element may be screwed to different extents corresponding to an intended discharge stroke or to an axial starting position of the plunger. If the housing and/or the axial guide element allows a plurality of discrete rotational positions of the propulsion element, e.g., if the propulsion element can be guided through the housing in a first orientation and in a second orientation, which is rotated by 180° or even only by 90° about the longitudinal axis with respect to the first orientation, a partial discharge stroke can be adjusted with a resolution of less than one thread turn, such as a half or a quarter of a thread turn.

Furthermore, the drive element may include a threaded rod with an external thread and the propulsion element may include a propulsion sleeve with the axial guide element and an internal thread adapted to the external thread. The internal thread may extend over a length corresponding to the maximum discharge stroke, and the external thread may be shortened to a few windings at a proximal end of the threaded rod or may include a threaded segment of less than one winding. Alternatively, for instance where the threaded rod or portions thereof are injection molded, the external thread extends over the maximum length of the discharge stroke and the internal thread may be correspondingly shortened. When the threaded rod rotates, the non-rotatingly mounted propulsion sleeve may be pushed in the distal direction, which may be easier to accomplish than a linear guidance of a threaded rod.

The torsion spring as an elastic means for generating a torque may be a spiral spring but may also be configured as a leaf spring, mainspring, conical spring, helical torsion spring, torsion bar, or combinations thereof. The torsion spring may be maximally or sufficiently pretensioned for a one-time discharge of the entire or at least a predetermined content of the product container when the autoinjector is delivered or before the autoinjector is operated. Accordingly, the autoinjector may not have a dose selection mechanism. A pre-filled, disposable, ready-to-use syringe may include the product container and an injection needle non-detachably fastened thereto and may be held axially fixedly in the housing of the autoinjector. The autoinjector, or at least the ready-to-use syringe and the syringe holder, may accordingly be provided as a single use component.

In implementations, the coupling may include a coupling sleeve with inwardly directed teeth or projections as first coupling elements, which may engage radially in second coupling elements, which may be coupled to the drive element in a rotationally fixed manner or integrally formed therewith. The second coupling elements may include outwardly directed teeth or recesses on the drive element or on a spring shaft coupled in a rotationally fixed manner to the drive element and the torsion spring. The coupling sleeve may be an independent component of the autoinjector and may not include any locking members for locking a needle protection sleeve in a needle protection position after an injection has taken place.

In implementations, the coupling sleeve may include a holding element, which may be released by an actuation movement or an actuation stroke of the needle protection sleeve. Subsequently, a spring, such as a needle protection spring, may move the coupling sleeve with the first coupling elements axially in a coupling stroke and in the proximal direction relative to the second coupling element, and the drive element may be released. The coupling stroke of the coupling sleeve may be limited by a distally directed stop on the mechanism holder, as a result of which an acoustic signal may be generated, which may signal the start of the discharge process to the user.

In implementations, one end of the torsion spring may be coupled to a shaft of a spring shaft in a rotationally fixed manner, and a spring flange may distally delimit an accommodation region or a volume of the torsion spring. The second coupling elements may be spaced apart from the distal spring flange by at least the length or amplitude of the coupling stroke and may be arranged on a widening, coupled to the drive element in a rotationally fixed manner, of the spring shaft including a sleeve or a flange.

In implementations, the coupling sleeve may be a locking sleeve and include a locking member for locking the needle protection sleeve in a needle protection position at the end of the injection. The second coupling elements may be arranged on a drive sleeve configured as a drive element, and its proximal end may be spaced apart from a distal spring flange by at least the length of the coupling stroke. The drive sleeve may be in a threaded engagement with a propulsion element, which may be configured as a piston rod.

In implementations, the drive sleeve and the locking sleeve may include a slide control system with a first guide element and second guide element, for example a radially aligned guide cam configured to engage in a guide groove. The guide elements may be configured to interact such that, after a release to cause rotation of the drive sleeve, an initial rotation of the drive sleeve by for instance at most 45° pushes the locking sleeve in the proximal direction by a locking stroke of at least 1 mm. This may ensure that the locking sleeve reliably reaches its locking position even in the case of the most unfavorable tolerances. The guide cam may be attached to the drive sleeve, and the guide groove may be provided in the locking sleeve and be aligned at an angle relative to the longitudinal axis.

The autoinjector may optionally include a permanently installed rotation sensor that may be configured for continuous detection of at least one rotational position per revolution of the drive element during the discharge process, as well as a processing unit that may be configured for determining an axial piston position of the piston in the product container or a residual volume in the product container from the successively detected rotational positions. A rotation of a drive member caused directly by the torsion spring during the discharge process may be measured continuously and with a resolution of half of a revolution or less, and the propulsion and the piston position may be determined therefrom. As a result of an improved resolution, for instance, the residual volume or the amount of medicament discharged may be precisely determined, which may facilitate situations where the discharge process does not proceed as planned or is even interrupted by the user. The progress of a discharge process may moreover be detected in real time, and fluctuations in the propulsion speed may be identified without delay.

The autoinjector furthermore may optionally include an optical, acoustic, or tactile signaling unit or an indicator unit with an electronically controlled actuator. The actuator may be controlled or activated by the processing unit after determining an axial piston position, which may correspond to an at least approximately complete discharge, and after subsequent expiry of a predetermined holding time. This may result in a signal being generated, which may indicate an end of the injection and may confirm to the user that the autoinjector can now be safely removed from the puncture site. Accordingly, the autoinjector may not have a purely mechanically triggered end-click, in which a stop element is accelerated by a spring. The holding time may typically be a few seconds, such as at least 3 seconds, and may ensure that the injected amount of medicament is completely absorbed or resorbed by the subcutaneous tissue and no liquid may pass through the puncture site onto the tissue surface after the autoinjector has been removed.

The autoinjector may include an electronics module with a printed circuit board and a sensor unit, arranged thereon, for detecting states or processes, a processing unit for processing signals of the sensor unit, a communication unit for wireless communication of data of the processing unit to a third-party device, and a battery for feeding the aforementioned units. Communication with a stationary third-party device, for example an expert system in a delocalized or cloud-based infrastructure, may take place, for example, via a 5G or 4G/LTE mobile radio network, such as a NarrowBand Internet-of-Things (NB-IoT). Communication with a mobile third-party device, for example a mobile phone or smartphone, or with a stationary gateway to a wired network, may take place via a Bluetooth or BLE connection, which may be initiated via an out-of-band pairing. The electronics module may furthermore include an optical, acoustic, and/or tactile indicator unit, such as an optical display, in which an optical waveguide guides the light of a light source on the printed circuit board to the surface of the housing. A state indicated by the indicator unit may comprise information regarding the medicament, a device state of the autoinjector, a module state of the electronics module, or a process state of an ongoing or completed injection process. The indicator unit of the electronics module may be a simplified indicator unit and for instance may include one or more (e.g., a few) LEDs, for example in traffic light colors or for illuminating selected pictograms, and/or to an acoustic signal generator for generating language-agnostic sounds or melodies. This may facilitate interaction with advanced graphical display options and voice output options of a computer device such as a smartphone since the computer device (e.g., smartphone) may be coupled wirelessly to the electronics module and may be responsible for handling more refined communications with the user beyond status indication.

BRIEF DESCRIPTION OF THE DRAWINGS

Implementations are described in connection with the appended figures, which are exemplary and are in no way to be interpreted as limiting. In the drawings.

DETAILED DESCRIPTION

The term "product," "medication", "medicament," or "medical substance" in the present disclosure includes any flowable medical formulation which is suitable for controlled administration by means of a cannula or hollow needle in subcutaneous or intramuscular tissue, for example a liquid, a solution, a gel, or a fine suspension containing one or more medical active ingredients. A medication or medicament can thus be a composition with a single active ingredient or a premixed or co-formulated composition with a plurality of active ingredients from a single container. The term includes in particular drugs, such as peptides (e.g., insulins, insulin-containing medicaments, GLP-1-containing preparations as well as derived or analogous preparations), proteins and hormones, biologically obtained or active ingredients, active ingredients based on hormones or genes, nutrient formulations, enzymes, and other substances both in solid (suspended) or liquid form. The term also includes polysaccharides, vaccines, DNA or RNA or oligonucleotides, antibodies or parts of antibodies as well as suitable base substances, excipients, and carrier substances.

The term "distal" refers to a side or direction directed toward the front, piercing-side end of the administration apparatus or toward the tip of the injection needle. In contrast, the term "proximal" refers to a side or direction directed toward the rear end of the administration apparatus that is opposite the piercing-side end.

In the present disclosure, the term "injection system" or "injector" is understood to mean an apparatus in which the injection needle is removed from the tissue after a controlled amount of the medical substance has been dispensed. In contrast to an infusion system, the injection needle in an injection system or in an injector thus does not remain in the tissue for a longer period of several hours.

Figure 1:
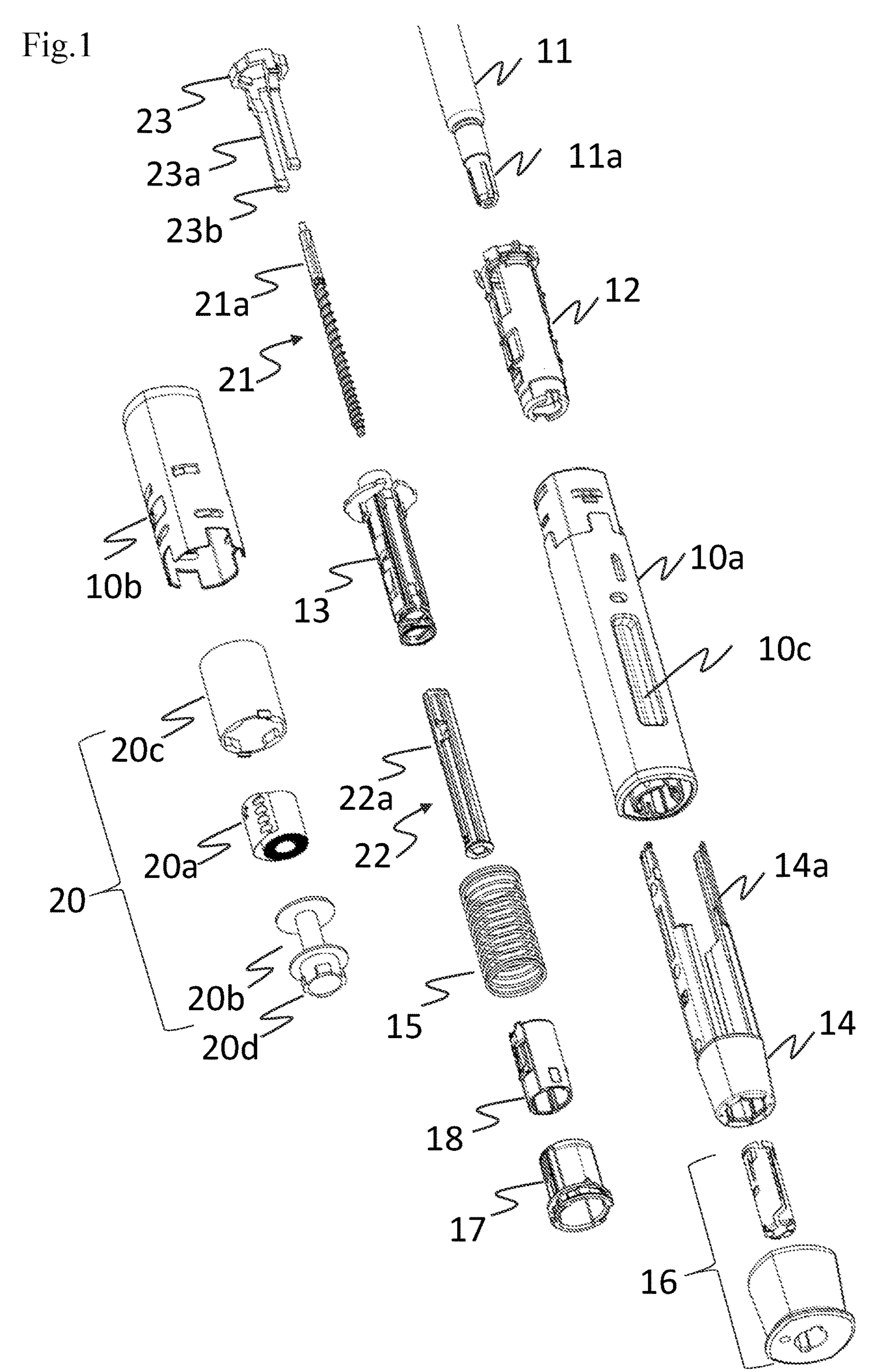
FIG. 1 shows the components of a first embodiment of an autoinjector, according to the present disclosure.

FIG. 1 is an exploded view of the components of an autoinjector according to a first embodiment of the present disclosure. The autoinjector includes a sleeve-shaped, elongated housing with a longitudinal axis L with a distal housing part 10*a* and a proximal end cap or closure cap 10*b*, which may be non-detachably snap-fitted therewith. The distal housing part 10*a* and the closure cap 10*b* may be configured with the same cross-section over the entire length of the autoinjector, and the closure cap 10*b* may include a single end face perpendicular to the longitudinal axis. A product container in the form of a single-use or ready-to-use syringe 11 with an injection needle non-detachably fastened to the product container may be held in a syringe holder 12, and the syringe holder 12 may be accommodated in the housing part 10*a* in an axially and rotationally fixed manner. The ready-to-use syringe 11 may be pressed in the distal direction into engagement with a shoulder of the syringe holder 12 by a retaining spring portion of a mechanism holder 13 fixedly anchored in the housing (e.g. in the closure cap 10*b*). In relation to the housing part 10*a*, the ready-to-use syringe 11 may be arranged such that the tip of the injection needle projects beyond the distal end of the housing part 10*a* by a length corresponding to the subcutaneous or intramuscular piercing depth and may at least be laterally protected or covered by a needle protection sleeve 14 before and after the injection. When the injection needle is inserted into the injection site along the longitudinal axis L, the needle protection sleeve 14 may be pushed in the proximal direction by an actuation stroke and against the force of a needle protection spring 15 and may thereby trigger a product discharge as described and shown herein. For this purpose, the needle protection sleeve 14 may include two sleeve arms 14*a* arranged offset or rotated by 90° about the longitudinal axis L with respect to two recesses 10*c* of the housing designated as viewing windows. After the injection has taken place, the needle protection sleeve 14 may be displaced relative to the housing 10 from the actuated position along the longitudinal axis L in the distal direction to a needle protection position where the needle protection sleeve 14 can be blocked against being pushed back again in the proximal direction. The needle protection spring 15 may be a spring constructed of metal, acts as a compression spring, and may be configured as a helical spring.

A spring pack 20 may include a rotation spring or torsion spring 20*a*, a spring shaft 20*b*, and a spring sleeve 20*c*. The outer end of the torsion spring 20*a* may be anchored in a rotationally fixed manner to the spring sleeve 20*c*, which in turn may be accommodated in a rotationally fixed manner in the housing part 10*a*. The outermost two windings of the torsion spring 20*a* may be tangentially fixed, for example welded, as a result of which the outermost winding itself acts as an integrated spring sleeve. The inner end of the torsion spring 20*a* may be connected to the spring shaft 20*b* in a rotationally fixed manner. The spring shaft 20*b* may include a shaft configured to receive the torsion spring 20*a* in the rotationally fixed manner and a distal and a proximal spring flange, which may axially delimit the spring volume. The spring pack 20 may be mounted as an independent component in the housing of the autoinjector in a pretensioned or fully pretensioned state and may accommodate torsion springs of different widths, as described in-depth in WO 2016/205963 A1, which is herein incorporated by reference in its entirety.

For ease of assembly, the autoinjector may be assembled from two subunits or assemblies. In this case, a distal syringe unit of the autoinjector may include a first, distal housing part 10*a*, the needle protection sleeve 14, the device cap 16, and the syringe holder 12, while a proximal drive unit may include the closure cap 10*b*, the mechanism holder 13, the needle protection spring 15, switching sleeve 17, locking sleeve 18, drive element and propulsion element, and the one-time or single-use loadable spring pack 20 for automatic substance delivery. In a filling or assembly process, the pre-filled or ready-to-use syringe 11 may be inserted into the distal syringe unit and the two subunits may be subsequently assembled, where the two housing parts, the distal housing part 10*a* and the closure cap 10*b*, may be non-detachably snap-fit. The outer end of the torsion spring 20*a* may be anchored to the spring sleeve 20*c* or, if no spring sleeve is provided, may be anchored to the mechanism holder 13 or directly to the closure cap 10*b*. A spring flange may also be fastened via its outer circumference to the spring sleeve 20*c*, to the mechanism holder 13, or to the housing.

The pre-filled or ready-to-use syringe 11 may include a cylindrical syringe body configured as a product container holding a product, at the distal end of which a hollow injection needle may be fixedly connected to a syringe shoulder. The injection needle of the ready-to-use syringe 11 may be covered by a needle protection cap 11*a*, which may be configured as a so-called rigid needle shield (RNS) and may include a rubber-elastic needle protection element and a sheath made of hard plastic. The needle protection cap may protect the injection needle against mechanical effects and contamination, and may keep the injection needle and the product sterile. At the distal end of the autoinjector, in the delivery state thereof, a pull-off cap or device cap 16 may be arranged, and axially pulled off and/or twisted off and completely removed along with the needle protection cap 11 a before the autoinjector is used. The syringe holder 12 may include two fingers, which may be fastened at their proximal ends to a holder sleeve of the syringe holder 12 and each may have, at their distal ends, an axial support element for the syringe shoulder. The syringe holder 12 shown may be adapted to the diameter of a ready-to-use syringe to be accommodated, with a nominal filling volume of 1.5 ml, 2.25 ml, or 4 ml, so that when the syringe size is changed, no components of the autoinjector except for the syringe holder 12 have to be replaced or at least the distal housing part 10*a* may be the same for all syringe sizes. For instance, for the smallest syringe diameter, the fingers may be flexible and may be pushed away radially by the needle protection cap when the ready-to-use syringe 11 is inserted axially. In order to accommodate a narrower syringe, the syringe holder 12 may also be configured in two parts or be supplemented by an adapter, as disclosed in WO 2020/164910 A1, which is herein incorporated by reference in its entirety.

The torsion spring 20*a* or the spring shaft 20*b* may set a drive element 21 into a rotational movement and a propulsion element 22 into a purely axial propulsion movement. For this purpose, a threaded element engages in a thread extending over the discharge stroke and having a variable thread pitch. The threaded element may include a threaded segment with a length in the rotational or circumferential direction of less than half a winding, where one flank of the threaded segment may have different pitch angles so that a different region of the flank of the threaded segment is in each case in contact with the thread when the thread pitch changes as the rotation progresses. The variable thread may have a greater pitch in the initial region of the discharge and a smaller pitch at the end so that, despite decreasing spring force, a constant discharge force results, as disclosed in WO 2016/205961 A1, which is herein incorporated by reference in its entirety.

A switching sleeve 17 may be arranged in a positive-locking manner with a proximal end of the sleeve arms 14*a* of the needle protection sleeve 14 and with a distal end of the needle protection spring 15 and may at least be partially surrounded by the latter. The switching sleeve 17 may be snap-fitted or even integrally formed with the proximal end of the sleeve arms 14*a* of the needle protection sleeve 14. A locking sleeve 18 may be arranged within and coaxially with the switching sleeve 17 and may be coupled to the switching sleeve 17 via a saw tooth-shaped locking member 18*a* (FIG. 5), which may be resiliently attached to an arm pointing in the distal direction, in such a way that an actuation movement of the needle protection sleeve 14 and the switching sleeve 17 also moves the locking sleeve 18 proximally. By means of an additional proximal locking stroke of the locking sleeve 18 relative to the switching sleeve 17 into a proximal end position, the locking member 18*a* may be reliably released by the switching sleeve 17 for movement inward. Due to the spring effect of the arm, the locking member 18*a* may engage behind a proximally directed edge of the autoinjector or latch into an axially fixed recess of the autoinjector and may thus lock the locking sleeve 18 against a distal movement. When the autoinjector is removed from the puncture site, the switching sleeve 17 may be pushed by the needle protection spring 15 in the distal direction over the locking member 18*a*, whereupon, as a result of the spring effect of the arm, the locking member 18*a* engages behind a proximally directed edge of the switching sleeve 17 in a locking position and locks or blocks the switching sleeve 17 and the needle protection sleeve 14 against renewed movement in the proximal direction.

In order to adjust a piercing depth in a range of 5 to 8 mm, and for instance to shorten it, suitably attached short axial ribs or projections on one of the two stop components may in this case define the proximal stop of the needle protection sleeve 14 on the housing or the proximal stop of the switching sleeve 17 on the mechanism holder 13. For such an adaptation of the piercing depth, at least one coupling element interacting with the needle protection sleeve 14 and/or a trigger element attached to the switching sleeve 17 may accordingly also have to be axially adapted or replaced for the correct triggering of the discharge.

The syringe holder 12 may be constructed of a transparent material so that the content of the syringe (e.g., the product contained therein) may be visually inspected through the viewing windows provided as recesses 10*c* in the housing part 10*a*. A magnifying glass formed in the region of the viewing window by a variable thickness in the material of the syringe holder 12 may allow suspended particles in the liquid product to be identified and the medicament state to be assessed. In order to protect the liquid from sunlight, an overlong device cap extending over the region of the viewing windows into the proximal half of the autoinjector may be provided.

In the first embodiment according to FIG. 1, the autoinjector includes a drive element 21 or a rotational member in the form of a threaded rod 21*a* with an external thread, which extends at least over a length corresponding to the discharge stroke. The threaded rod 21*a* may be coupled to the spring shaft 20*b* in a rotationally fixed manner or may even be integrally formed therewith. A propulsion element in the form of a propulsion sleeve 22*a* has, at a proximal end on an inner side, a threaded element for engagement in the external thread of the threaded rod 21*a*, including a threaded portion with fewer windings than the external thread, or a threaded segment with a length in the direction of rotation of less than one winding, such as less than half a winding. The propulsion sleeve 22*a* in the mechanism holder 13 or in the housing may be secured against rotation by an axial groove or by another structural deviation from a rotationally symmetrical outer side, such that the rotation of the drive element generated by the torsion spring 20*a* is converted into a linear propulsion movement of the propulsion sleeve 22*a*. Alternatively, the propulsion sleeve 22*a* may have an internal thread, which may extend over a length corresponding to the discharge stroke, and the thread of the threaded rod 21*a* may be reduced to a threaded element for engagement in the internal thread, and may include a threaded portion with fewer windings than the internal thread, or a threaded segment having a length of less than one winding, such as less than half a winding. A coupling sleeve 23 may be configured with a hollow cylindrical body and a holding element with two flexible holding arms 23*a*, which may extend in the distal direction and at the distal end of which a radially inward standing holding cam 23*b* is located in each case. The spring shaft 20*b* may include a distal widening 20*d* including a sleeve arranged concentrically with the spring shaft 20*b* and may include locking surfaces 24*a*, configured to act tangentially against rotation about the longitudinal axis and may be directed radially outward, on four protrusions distributed over the circumference of the sleeve. The locking surfaces 24*a* may also be formed by indentations on the periphery of a flange of the widening 20*d* arranged concentrically with the spring shaft 20*b*.

Figure 2:
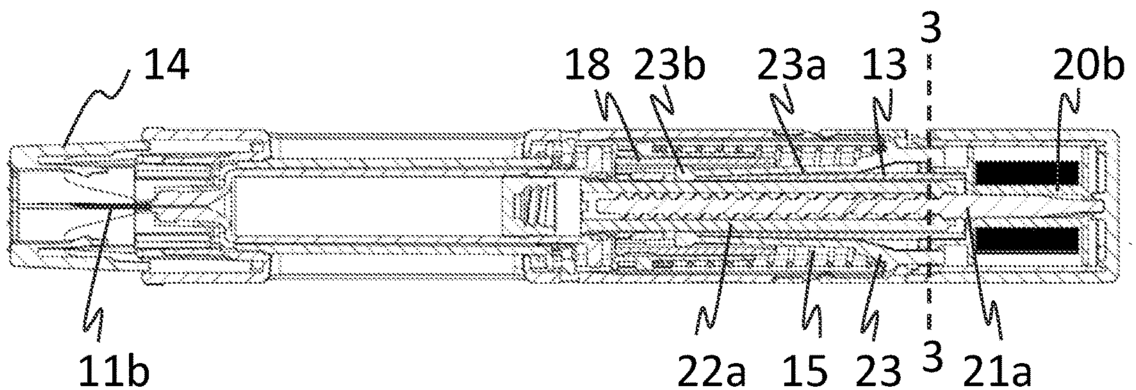
FIG. 2 shows a longitudinal cross-section through the autoinjector of FIG. 1 before injection.

FIG. 2 shows a longitudinal section through the autoinjector according to FIG. 1 after removal of the device cap, in the injection-ready state, in which the injection needle llb is covered laterally by the needle protection sleeve 14. Before discharge, the holding cams 23*b* of the holding element may engage in recesses of the axially fixed mechanism holder 13 and are prevented from moving outward by an inner circumference of the locking sleeve 18, as a result of which the coupling sleeve 23 also cannot move axially. When the discharge is triggered, the locking sleeve 18 is moved away from the position of the recesses by a proximal movement of the needle protection sleeve 14 so that the holding arms 23*a* can detach radially and release the coupling sleeve 23.

Figure 3:
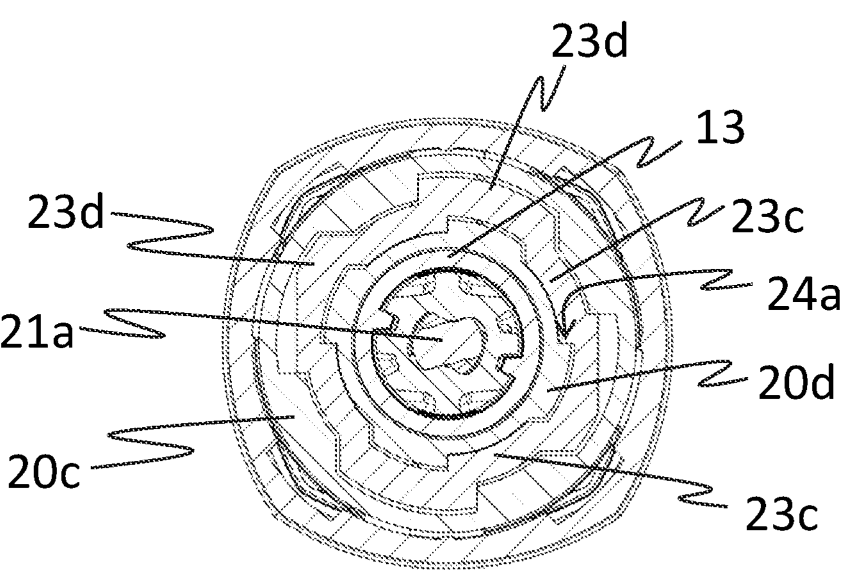
FIG. 3 shows a cross-section through the autoinjector of FIG. 1 at line 3-3 of FIG. 2.

FIG. 3 shows a cross-section through the autoinj ector axially at the level of a proximal end of the coupling sleeve 23 before discharge, indicated by an interrupted vertical line 3-3 in FIG. 2. At this point, the coupling sleeve 23 includes four projections 23*c*, each offset by 90° and directed inward, as the first coupling element, which may engage in a rotationally fixed manner via radially aligned locking surfaces 24*a* in four corresponding recesses on a distal widening 20*d* of the spring shaft 20*b* as the second coupling element. At the same time, four protrusions 23*d* of the coupling sleeve 23 distributed uniformly over the circumference and directed outward, engage in four recesses of a spring sleeve 20*c* mounted in a rotationally fixed manner in the housing. The projections 23*c* and protrusions 23*d* have an angular separation by approximately 45°, and the inward directed projections 23*c* are moreover offset against the outward directed protrusions 23*d*, resulting in a more or less constant thickness of the coupling sleeve 23. As can be seen in FIG. 3, the projections/protrusions of the coupling sleeve 23 arranged alternately inside and outside may also be referred to as recesses/indentations of the coupling sleeve 23 arranged on alternate sides. The spring shaft 20*b* may be coupled to the housing such as to the closure cap 10*b* in a rotationally fixed manner by the two engagements, so neither the threaded rod 21*a* nor the propulsion sleeve 22*a* can move.

Figure 4:
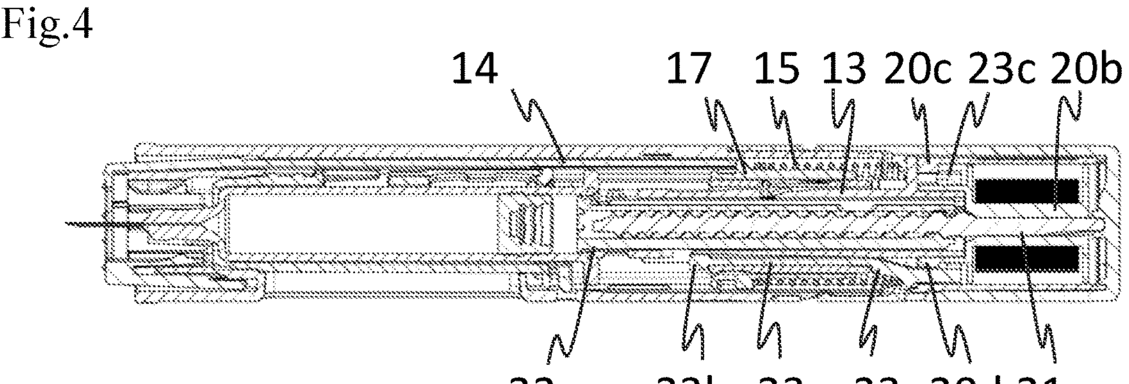
FIG. 4 shows a longitudinal cross-section through the autoinjector of FIG. 1 during injection.

FIG. 4 depicts a combined longitudinal section through the autoinj ector immediately after triggering or at the beginning of the discharge process. The sectional plane of the lower half corresponds to the sectional plane of FIG. 2 and is rotated about the longitudinal axis by 60° with respect to the sectional plane of the upper half. The needle protection sleeve 14 is displaced proximally as a result of contact with the injection site and thereby also pushes the locking sleeve 18 in the proximal direction while tensioning the needle protection spring 15. The holding arms 23*a* of the coupling sleeve 23 may thereby be released radially outward for a first release movement, and the coupling sleeve 23 can move axially. The proximal end of the needle protection spring 15 may be supported on the coupling sleeve 23 and may proximally push it by a coupling stroke, where the coupling stroke in this embodiment differs from the actuation stroke of the needle protection sleeve 14. In this case, the locking sleeve 18, along with the mechanism holder 13, may be moved proximally with respect to the switching sleeve 17 over radially outward directed projections on the holding arms 23*a* to a first stop by a locking stroke corresponding to the coupling stroke. In this end position of the locking sleeve 18, the locking of the needle protection sleeve 14 is activated in that the locking member 18*a* latches with an inward directed projection into a recess of the mechanism holder 13 and prevents a distal movement of the locking member 18*a*. If the first stop takes place not by the coupling sleeve 23 but by the locking sleeve 18, the coupling sleeve 23 is available at the end of the discharge process for a final stroke up to a second stop and thus for a mechanical end-click. For this purpose, the holding arms 23*a* may be released radially inward from a proximal end edge of the propulsion sleeve 22*a* for a second release movement. Since the locking surfaces of the inner projections 23*c* of the coupling sleeve 23 and of the recesses of the widening 20*d* of the spring shaft 20*b* each have an axial length, abutment area or an overlap of less than the coupling stroke, the engagements of the projections 23*c* of the coupling sleeve 23 with the recesses of the widening 20*d* may thereby be released, and the spring shaft 20*b* may start to rotate under the effect of the torsion spring 20*a*. The locking surfaces of the widening 20*d* of the spring shaft 20*b* may be located on indentations of a flange which is at a distance of at least the coupling stroke from the distal spring flange in the distal direction, or on formations, e.g., protrusions, on a sleeve which may be at a distance of at least the coupling stroke from the distal spring flange in the distal direction.

Figure 5:
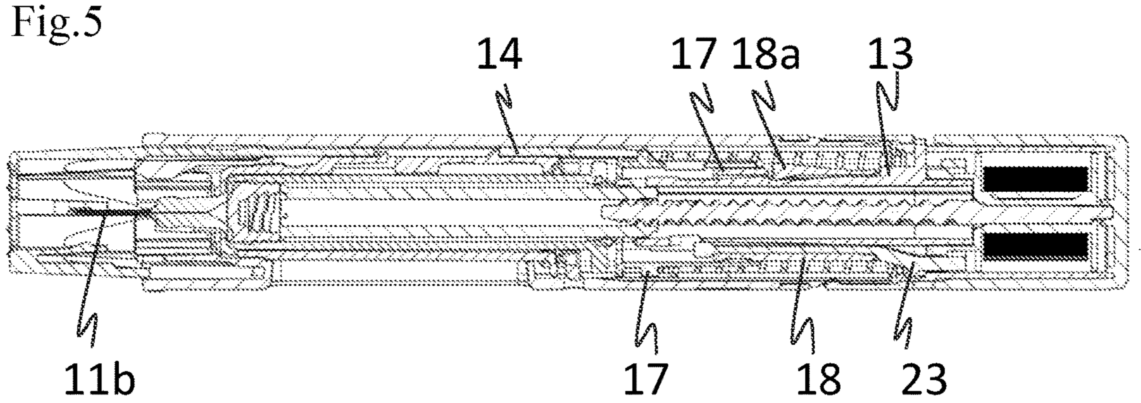
FIG. 5 shows a longitudinal cross-section through the autoinjector of FIG. 1 after injection.

FIG. 5 depicts a combined longitudinal section through the autoinjector after injection. The sectional plane of the lower half corresponds to the sectional plane of FIG. 2 and is rotated about the longitudinal axis by 90° with respect to the sectional plane of the upper half. The needle protection sleeve 14, which is moved in a securing movement during removal of the autoinjector from the puncture site from a rear end position into a front end position by a needle protection spring 15, laterally covers the injection needle 11*b*. The radially inwardly directed projections on resilient arms of the locking member 18*a* of the locking sleeve 18 may engage in recesses of the mechanism holder 13, whereby a movement of the locking sleeve 18 in at least the distal direction is prevented. The locking sleeve 18 rests proximally on a distal end face of the mechanism holder 13 so that the locking sleeve 18 also cannot move in the proximal direction. Radially outward directed projections on the resilient arms of the locking member 18*a* may engage behind a proximal edge of the switching sleeve 17 so that the switching sleeve 17 likewise cannot be moved in the proximal direction. The axially fixed locking of the locking sleeve 18 may also or alternatively take place by a locking element or snap element that is different from the locking sleeve 18.

The inner and the outer embossments of the coupling sleeve 23 and of their respective counterparts may differ in configuration, number, and/or axial arrangement. For example, the protrusions may assume the shape of axial ribs, and the recesses on the spring shaft 20*b* or spring sleeve 20*c* may accordingly assume the shape of axial slots or grooves, or both protrusions and recesses may be formed as teeth. The recesses on the spring sleeve 20*c* may also be attached directly to the housing; the corresponding connection may, but does not have to be released during the coupling stroke. In view of the single-use configuration of the autoinjector and of the rotation blocking, the inner and outer protrusions of the coupling sleeve 23 may also each be configured differently from one another as long as the axial length and arrangement of the inner projections permits release of the engagement by a coupling stroke and the outer protrusions are compatible with the rotational alignment of the holding arms 23*a* of the coupling sleeve 23.

Figure 6:
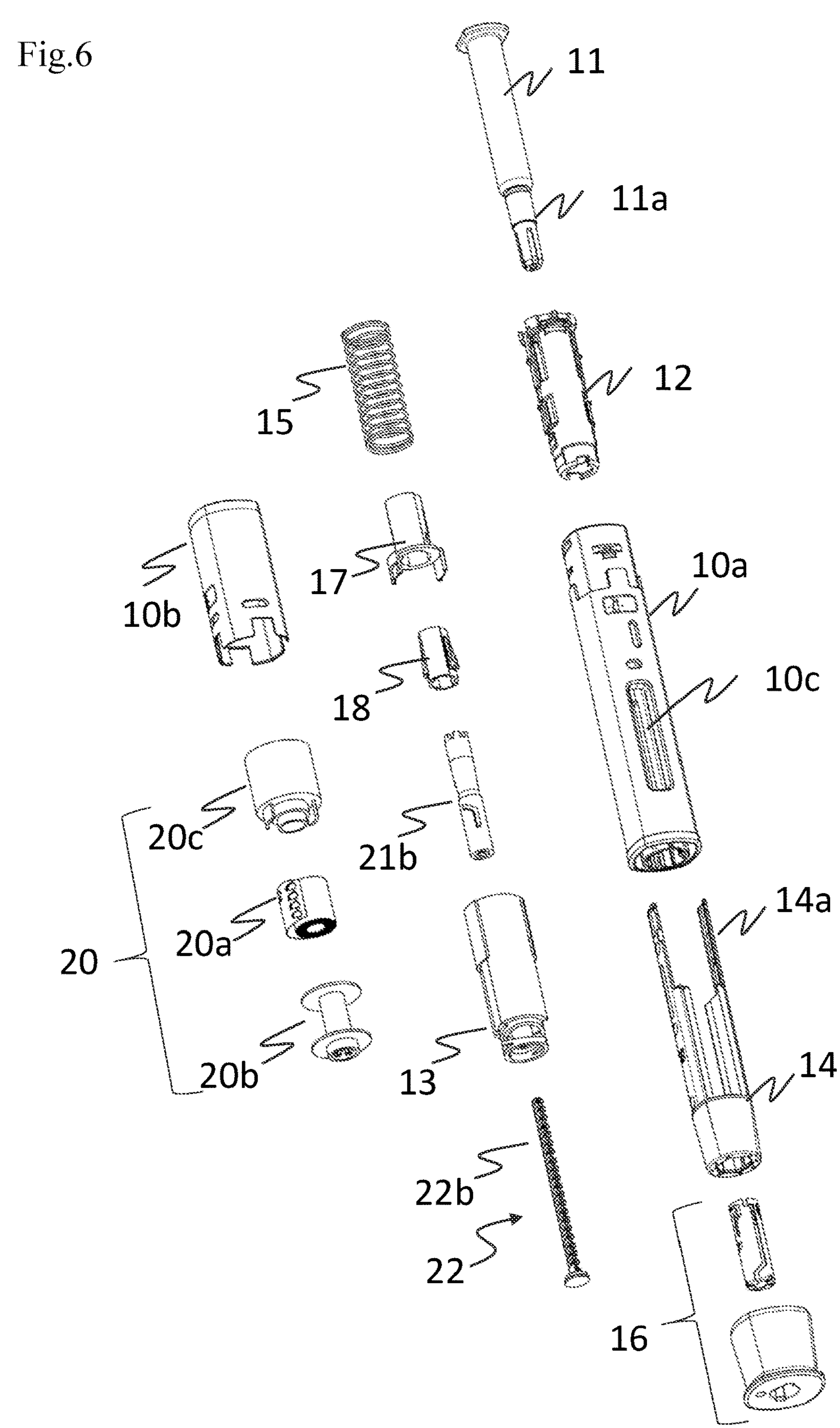
FIG. 6 shows the components of a second embodiment of an autoinjector, according to the present disclosure.

FIG. 6 is an exploded view of the components of an autoinjector according to a second embodiment of the present disclosure. The components different in comparison to FIG. 1 include a drive element 21 in the form of a drive sleeve 21*b*, which may be connected in a rotationally and axially fixed manner distally of the torsion spring 20*a*, to the spring shaft 20*b* or may even be integrally formed therewith. At its distal end, the drive sleeve 21*b* may include a threaded element, which may engage in an external thread, extending over a length corresponding to the discharge stroke, of a piston rod 22*b*. The threaded element of the drive sleeve 21*b* may include a threaded portion of an internal thread with fewer windings than the external thread of the piston rod 22*b*, or a threaded segment with a length in the direction of rotation of less than one winding, such as less than half a winding. The piston rod 22*b* may be located in an interior of the drive sleeve 21*b* and may serve as a propulsion element; it may include a longitudinal groove into which the mechanism holder 13 fixed to the housing engages so that a purely axial forward movement of the piston rod 22*b* may result in a known manner from a rotational movement of the drive sleeve 21*b*. Alternatively, the sleeve-shaped drive sleeve 21*b* may have an internal thread which extends over a length corresponding to the discharge stroke, and the thread of the piston rod 22*b* at the proximal end may be reduced to a threaded portion having a few windings or may include a threaded segment of less than one winding.

Figure 7:
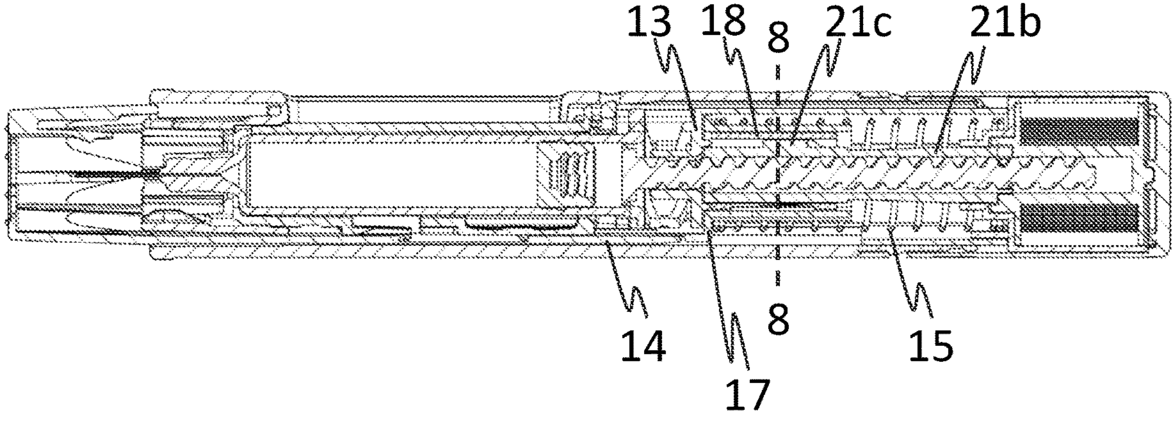
FIG. 7 shows a longitudinal cross-section through the autoinjector of FIG. 6 before injection.

FIG. 7 shows a combined longitudinal section through the autoinj ector according to FIG. 6 in the injection-ready state, after removal of the device cap 16. The sectional plane of the lower half is rotated by 90° about the longitudinal axis with respect to the sectional plane of the upper half. The switching sleeve 17, which may be pushed by the needle protection spring 15 in the distal direction against a proximal end of the needle protection sleeve 14, may be guided in a rotationally fixed manner in the mechanism holder 13. The locking sleeve 18 may be coupled to the switching sleeve 17 in a rotationally fixed manner. On its outer side, the drive sleeve 21*b* may include a protrusion, as the second coupling element, in the form of two opposite axially aligned locking ribs 21*c*.

Figures 8, 10:
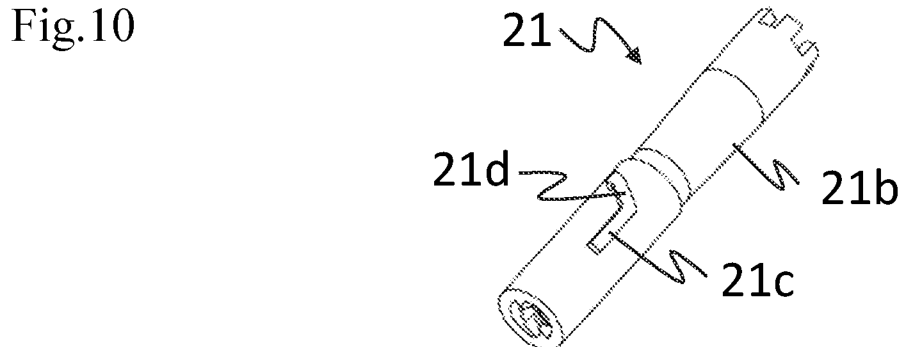
FIG. 8 shows a cross-section through the autoinjector of FIG. 6 at line 8-8 of FIG. 7.
FIG. 10 shows a drive element of the autoinjector of FIG. 6.

Distally in the viewing direction, FIG. 8 shows a cross-section through the autoinjector axially at the level of the protrusions of the drive sleeve 21*b*, indicated in FIG. 7 by an interrupted vertical line 8-8. At this point, the locking sleeve 18 may include two locking grooves into which the locking ribs 21*c* engage via locking surfaces 24*b* and which may prevent or block a rotation of the drive sleeve 21*b* at least in the direction of expansion of the torsion spring (counter-clockwise in the viewing direction of FIG. 8) and thus a propulsion of the piston rod 22*b*. The engagement may be released and the drive sleeve 21*b* released for rotation by an axial movement of the locking sleeve 18 during piercing by a coupling stroke, which may correspond to the actuation stroke in this embodiment.

As an alternative to the illustrated engagement by means of two locking ribs/locking grooves, other protrusions or projections on the drive sleeve 21*b* may also serve as the second coupling element and engage in a rotationally fixed manner in corresponding recesses or indentations of the locking sleeve 18 as the first coupling element, provided that the engagement of the locking surfaces become separated during the coupling stroke of the locking sleeve 18 (e.g., axially and/or lengthwise).

Figure 9:
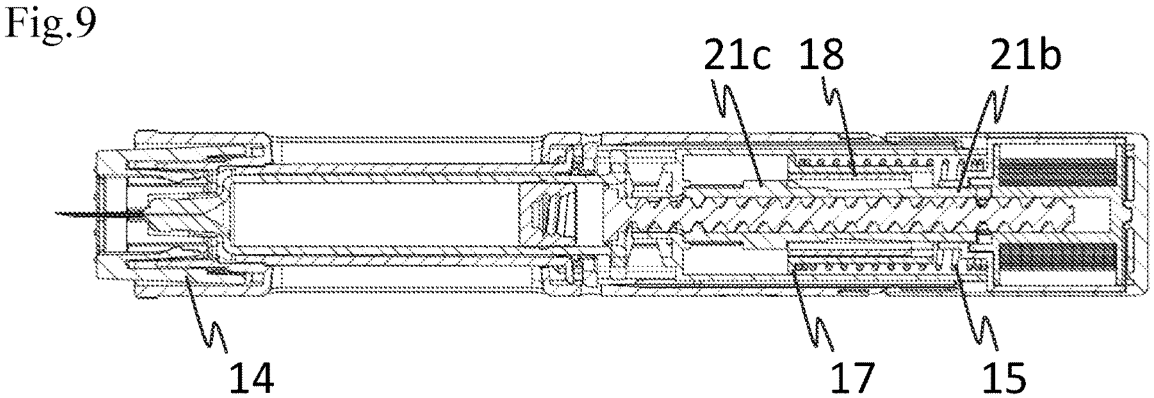
FIG. 9 shows a longitudinal cross-section through the autoinjector of FIG. 6 during injection.

FIG. 9 shows a longitudinal section through the autoinj ector immediately after triggering or at the beginning of the discharge process. The needle protection sleeve 14 may be displaced proximally as a result of contact with the injection site and may thereby also push the switching sleeve 17 and the locking sleeve 18 in the proximal direction while tensioning the needle protection spring 15 and releasing the drive sleeve 21*b* as described.

The drive sleeve 21*b* may have a further protrusion in the form of a pin or cam, which after the coupling stroke has taken place, engages as the first guide element in a second guide element in the form of a guide groove of the locking sleeve 18. These guide elements, may be configured as a slide control system, and have the effect that an initial rotation of the drive sleeve 21*b* moves or slides the locking sleeve 18 with respect to the switching sleeve 17 by a locking stroke further proximally into an end position of the locking sleeve 18 in which the locking of the needle protection sleeve 14 is activated in that the locking member 18*a* latches with an inward directed projection into a circumferential groove of the axially fixed drive sleeve 21*b*. The axial end position of the locking sleeve 18 assumed in this case can be seen in FIG. 9; in this position, the locking sleeve 18 is axially locked. The guide groove of the locking sleeve 18 is not oriented in parallel to the longitudinal axis of the autoinjector or is angled in this respect or is configured in the form of a helical line portion.

FIG. 10 shows an embodiment of the first guide element 21*d* in the form of an angled elongation may be arranged in the proximal direction of a protrusion which forms the locking rib 21*c*. The region of the elongation of the guide element 21*d* is angled with respect to the longitudinal axis; accordingly, the locking groove of the locking sleeve 18 shown in FIG. 8 may be configured to be wide enough such that it, as the second guide element, can likewise accommodate the elongation of the guide element 21*d*. Toward the end of the coupling stroke, as soon as the axial locking rib 21*c* exits axially from the locking groove of the locking sleeve 18 and decouples the locking surfaces 24*b*, the drive sleeve 21*b*, and thus a surface, angled with respect to the longitudinal axis, of the elongation of the guide element 21*d*, start to rotate. The locking sleeve 18 is thereby pushed further in the proximal direction, and relative to the switching sleeve 17, until the locking member of the locking sleeve 18 latches behind a circumferential edge of the drive sleeve 21*b* and makes a movement of the locking sleeve 18 in the distal direction impossible. The guide element 21*d* does not have to directly adjoin the locking rib 21*c*, but may also be offset in the circumferential direction and move in a separate guide groove different from the locking groove.

Figure 11:
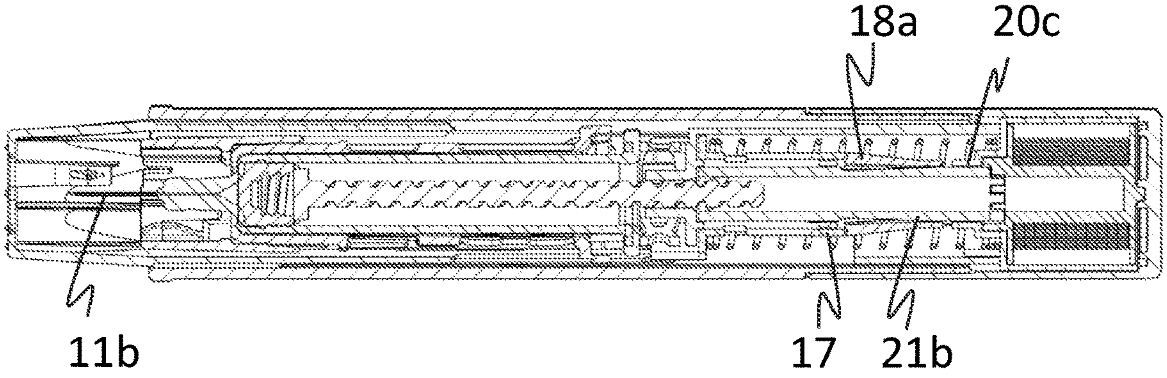
FIG. 11 shows a longitudinal section through the autoinjector of FIG. 6 after injection.

FIG. 11 shows a longitudinal section through the autoinjector after injection. The needle protection sleeve 14, which is moved in a securing movement during removal of the autoinjector from the puncture site from a rear end position into a front end position by a needle protection spring 15, laterally covers the injection needle 11*b*. The locking member 18*a* with radially inward directed projections on resilient arms of the locking sleeve 18 engages in a circumferential recess of the drive sleeve 21*b*, thereby preventing movement of the locking sleeve 18 in at least the distal direction. The locking sleeve 18 rests proximally on a distal end face of the spring sleeve 20*c* so that the locking sleeve 18 also cannot move in the proximal direction. Radially directed projections on the resilient arms engage behind a proximal edge of the switching sleeve 17 so that the switching sleeve 17 likewise cannot be moved in the proximal direction.

| LIST OF REFERENCE SIGNS | |
|---|---|
| 10a | Housing part |
| 10b | Closure cap |
| 10c | Recess |
| 11 | Ready-to-use syringe |
| 11a | Needle protection cap |
| 11b | Injection needle |
| 12 | Syringe holder |
| 13 | Mechanism holder |
| 14 | Needle protection sleeve |
| 14a | Arm |
| 15 | Needle protection spring |
| 16 | Device cap |
| 17 | Switching sleeve |
| 18 | Locking sleeve |
| 18a | Locking member |
| 20 | Spring pack |
| 20a | Torsion spring |
| 20b | Spring shaft |
| 20c | Spring sleeve |
| 20d | Widening |
| 21 | Drive element |
| 21a | Threaded rod |
| 21b | Drive sleeve |
| 21c | Locking Rib |
| 21d | Guide element |
| 22 | Propulsion element |
| 22a | Propulsion sleeve |
| 22b | Piston rod |
| 23 | Coupling sleeve |
| 23a | Holding arm |
| 23b | Holding cam |
| 23c | Projection |
| 23d | Protrusion |
| 24a, b | Locking surface |

What is claimed is:

1. An autoinjector, comprising:

a housing;

a product container axially fixed in the housing;

a torsion spring;

a drive element;

a propulsion element; and a needle protection sleeve, wherein, when the autoinjector is pressed against an injection site, the needle protection sleeve carries out an actuation movement in a proximal direction, wherein, for discharging liquid from the product container through an injection needle into the injection site, the torsion spring causes the drive element to rotate, wherein rotation of the drive element causes a movement of the propulsion element and of a piston in the product container in a distal direction, wherein the autoinjector comprises a coupling, which does not include the propulsion element and which is adapted to release the drive element for rotation as a result of the actuation movement of the needle protection sleeve, and wherein the coupling comprises a first coupling element configured to engage via a locking surface with a second coupling element in an engagement, wherein prior to the actuation movement, the engagement blocks the rotation of the drive element, and wherein during the actuation movement, an axial coupling stroke causes the engagement to be released such that one of the first coupling element or the second coupling element rotates relative to the other during the rotation of the drive element.

2. The autoinjector according to claim 1, wherein a length of the axial coupling stroke corresponds to a piercing depth of the injection needle.

3. The autoinjector according to claim 1, wherein the propulsion element comprises an axial guide for an exclusively linear propulsion movement in the housing.

4. The autoinjector according to claim 3, wherein the drive element comprises a threaded rod and the propulsion element comprises a propulsion sleeve.

5. The autoinjector according to claim 4, wherein the coupling comprises a coupling sleeve with the first coupling element configured to engage radially in the second coupling element coupled to the drive element in a rotationally fixed manner.

6. The autoinjector according to claim 5, wherein the coupling sleeve comprises a holding element configured to be released by the actuation movement of the needle protection sleeve, and wherein the autoinjector further comprises a spring, and upon release of the holding element, the spring is configured to move the coupling sleeve axially relative to the second coupling element in the axial coupling stroke.

7. The autoinjector according to claim 5, wherein one end of the torsion spring is configured to be rotationally fixedly coupled to a spring shaft and a spring flange distally delimits an accommodation region of the torsion spring, and wherein the second coupling element is arranged on a widening of the spring shaft and is spaced apart from the distal spring flange by at least a length of the axial coupling stroke.

8. The autoinjector according to claim 1, wherein the first coupling element and the second coupling element comprise at least two locking surfaces on protrusions or corresponding recesses.

9. The autoinjector according to claim 1, further comprising a rotation sensor configured to detect at least one rotational position per revolution of the drive element during a discharge process, and a processor unit configured to determine an axial piston position of the piston in the product container based on detected rotational positions of the drive element.

10. The autoinjector according to claim 9, further comprising a communication unit configured to communicate with at least one of a third-party device or an indicator unit configured to indicate a state of the autoinjector.

11. An autoinjector, comprising:

a housing;

a product container axially fixed in the housing;

a torsion spring;

a drive element;

a propulsion element;

a needle protection sleeve; and a locking sleeve, wherein, when the autoinjector is pressed against an injection site, the needle protection sleeve carries out an actuation movement in a proximal direction, wherein, for discharging liquid from the product container through an injection needle into the injection site, the torsion spring causes the drive element to rotate, wherein rotation of the drive element causes a movement of the propulsion element and of a piston in the product container in a distal direction, wherein the autoinjector comprises a coupling, which does not include the propulsion element and which is adapted to release the drive element for rotation as a result of the actuation movement of the needle protection sleeve, and wherein the coupling comprises a first coupling element configured to engage via a locking surface with a second coupling element in an engagement, wherein prior to the actuation movement, the engagement blocks the rotation of the drive element, wherein during the actuation movement, an axial coupling stroke causes the engagement to be released such that one of the first coupling element or the second coupling element rotates relative to the other during the rotation of the drive element, and wherein the locking sleeve comprises a locking member for locking the needle protection sleeve in a needle protection position at an end of the injection, wherein the first coupling element is arranged on the locking sleeve.

12. The autoinjector according to claim 11, wherein the drive element comprises a drive sleeve and the propulsion element comprises a piston rod, and wherein drive sleeve comprises the second coupling element.

13. The autoinjector according to claim 12, wherein the drive sleeve comprises a first guide element and the locking sleeve comprises a second guide element, wherein the first guide element and the second guide element form a slide control system, and wherein the slide control system is configured such that an initial rotation of the drive sleeve pushes the locking sleeve in a proximal direction by a locking stroke.

14. The autoinjector according to claim 11, wherein a length of the axial coupling stroke corresponds to a piercing depth of the injection needle.

15. The autoinjector according to claim 11, wherein the propulsion element comprises an axial guide for an exclusively linear propulsion movement in the housing.

16. The autoinjector according to claim 15, wherein the drive element comprises a threaded rod and the propulsion element comprises a propulsion sleeve.

17. The autoinjector according to claim 16, wherein the coupling comprises a coupling sleeve with the first coupling element configured to engage radially in the second coupling element coupled to the drive element in a rotationally fixed manner.

18. The autoinjector according to claim 17, wherein the coupling sleeve comprises a holding element configured to be released by the actuation movement of the needle protection sleeve, and wherein the autoinjector further comprises a spring, and upon release of the holding element, the spring is configured to move the coupling sleeve axially relative to the second coupling element in the axial coupling stroke.

19. The autoinjector according to claim 17, wherein one end of the torsion spring is configured to be rotationally fixedly coupled to a spring shaft and a spring flange distally delimits an accommodation region of the torsion spring, and wherein the second coupling element is arranged on a widening of the spring shaft and is spaced apart from the distal spring flange by at least a length of the axial coupling stroke.

20. The autoinjector according to claim 11, wherein the first coupling element and the second coupling element comprise at least two locking surfaces on protrusions or corresponding recesses.

21. The autoinjector according to claim 11, further comprising a rotation sensor configured to detect at least one rotational position per revolution of the drive element during a discharge process, and a processor unit configured to determine an axial piston position of the piston in the product container based on detected rotational positions of the drive element.

22. The autoinjector according to claim 21, further comprising a communication unit configured to communicate with at least one of a third-party device or an indicator unit configured to indicate a state of the autoinjector.

* * * * *